United States Patent [19]
Varadaraj

[11] Patent Number: 6,046,362
[45] Date of Patent: Apr. 4, 2000

[54] RECOVERY OF AMINES FROM EMULSIONS

[75] Inventor: Ramesh Varadaraj, Flemington, N.J.

[73] Assignee: Exxon Research and Engineering Company, Florham Park, N.J.

[21] Appl. No.: 09/049,358

[22] Filed: Mar. 27, 1998

[51] Int. Cl.⁷ .................................................. C07C 209/00
[52] U.S. Cl. .............................................................. 564/497
[58] Field of Search ............................................ 564/497

[56] References Cited

U.S. PATENT DOCUMENTS 2,424,158  7/1947  Fuqua et al. .
4,752,381  6/1988  Ferguson et al. .

Primary Examiner—Samuel Barts
Attorney, Agent, or Firm—Estelle C. Bakun

[57] ABSTRACT

The instant invention is directed to a method for recovering surface active amines from an emulsion comprising the salt of the amine comprising (a) contacting an emulsion layer or phase containing surface active amine salt with an acid selected from the group comprising mineral acids and carbon dioxide in an amount sufficient and under conditions to produce an amine salt of said mineral acid or an amine bicarbonate, wherein said surface active amine salt is produced via emulsion fractionation with said surface active amine (b) separating an upper layer and a lower aqueous layer; (c) adding, to the lower aqueous layer, an inorganic base if step (a) utilizes a mineral acid, or heating at a temperature and for a time sufficient if step (a) utilizes carbon dioxide, to raise the pH of the aqueous layer to greater than or equal to 8; (d) blowing gas through said aqueous layer to produce a foam containing said surface active amine; (e) recovering said foam containing said surface active amine.

6 Claims, 1 Drawing Sheet

RECOVERY OF AMINES FROM EMULSIONS

FIELD OF THE INVENTION

The instant invention is directed to the recovery of surface active amines from water-in-oil or oil-in-water emulsions comprised of the surface active amines.

BACKGROUND OF THE INVENTION

Emulsion fractionation processes are known in the art. For example, methods for treating crude oils using emulsion fractionation via formation of water-in-oil or oil-in-water emulsions are known. Specifically, acidic crude oils can be emulsion fractionated to remove, e.g., organic acids present in the crude.

What is needed in the art is a way to recover surface active amines from emulsions generated in such emulsion fractionation processes.

SUMMARY OF THE INVENTION

The instant invention is directed to a method for recovering surface active amines from an emulsion comprising the salt of the amine and naphthenic acid comprising (a) contacting an emulsion layer or phase containing surface active amine salt with an acid selected from the group comprising mineral acids or carbon dioxide in an amount sufficient and under conditions to produce an amine salt of said mineral acid or an amine bicarbonate, wherein said surface active amine salt is produced via emulsion fractionation with said surface active amine (b) separating an upper layer and a lower aqueous layer; (c) adding, to the lower aqueous layer, an inorganic base if step (a) utilizes a mineral acid, or heating at a temperature and for a time sufficient if step (a) utilizes carbon dioxide, to raise the pH of the aqueous layer to greater than or equal to 8; (d) blowing gas through said aqueous layer to produce a foam containing said surface active amine; (e) recovering said foam containing said surface active amine.

DETAILED DESCRIPTION OF THE INVENTION

Figure 1:
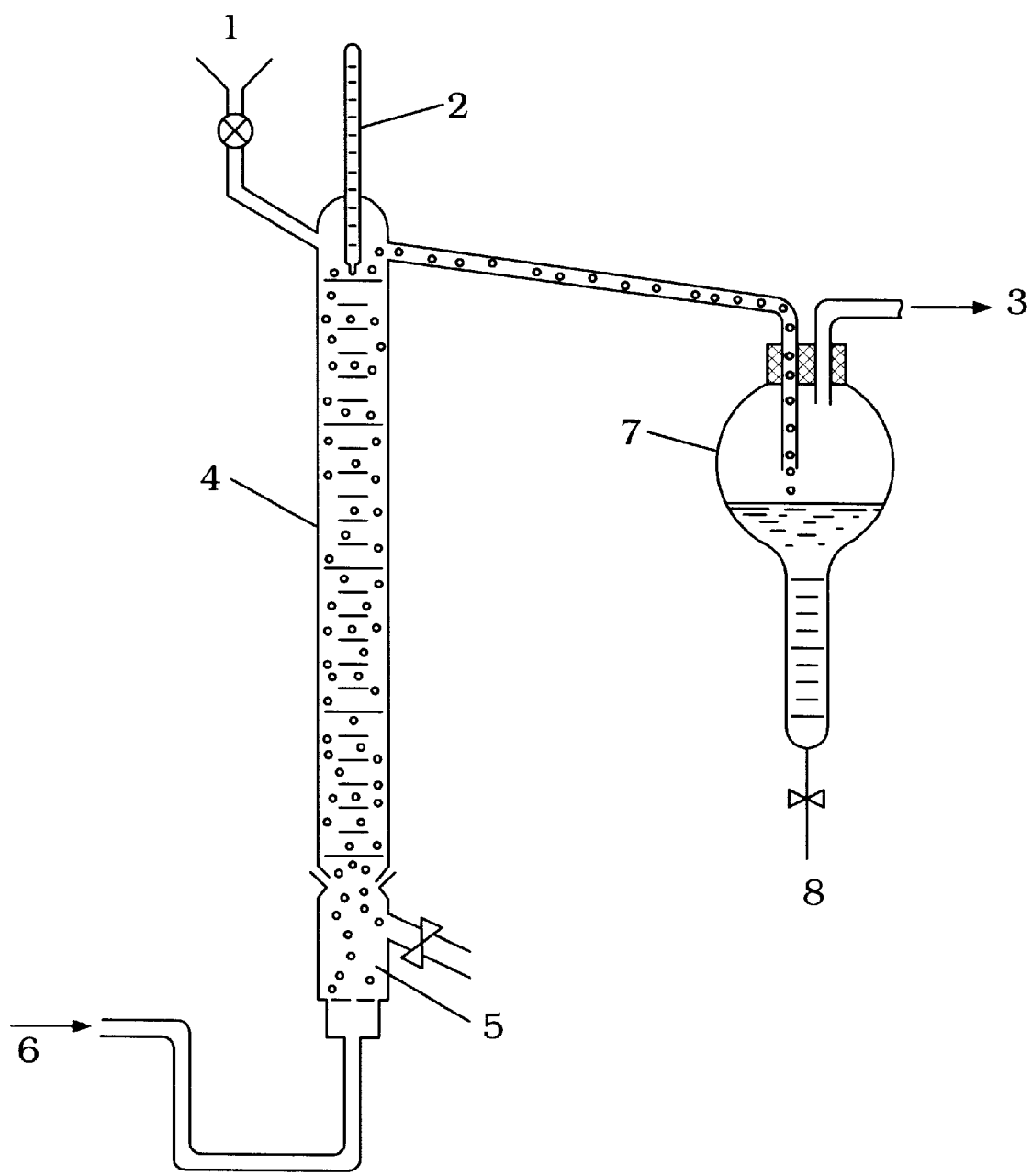
FIG. 1 is an apparatus useable in recovering ethoxylated amines that have been used to remove naphthenic acids from a starting crude. (1) is a layer or phase containing surface active amine, (2) is a thermometer, (3) is a vent, (4) is a graduated column for measuring foam height, (5) is a gas distributor, (6) is gas, (7) is where the foam breaks, and (8) where the recovered surface active amine is collected.

The instant invention is applicable for recovering any surface active amine utilzed in an emulsion fractionation process. Particularly, the instant invention is utilizable in recovering surface active amines utilized in emulsion fractionation of aqueous hydrocarbon containing streams, more particularly emulsion fractionation of crude oils to remove organic acids.

The invention is applicable to both production and refining crude oil applications where emulsion fractionation utilizing surface active amines can be employed.

The surface active amines capable of being recovered in the instant invention are any surface active amines. Particularly, alkyl oxyalkylated amines will be recovered. Preferably, the recovered amines will be alkyl ethoxylated or alkyl propoxylated amines, more preferably, alkyl ethoxylated amines.

The mineral acids utilized in the instant invention may be selected from sulfuric acid, hydrochloric acid, phosphoric acid and mixtures thereof. Additionally, carbon dioxide may be added to the emulsion of amine salt under pressure. In either scenario, the acid addition is continued until a pH of about 6 or less is reached, preferably about 4 to about 6. Acid addition results in formation of an upper layer, and a lower aqueous layer. The layers are then separated and to the aqueous layer is added an inorganic base such as ammonium hydroxide, sodium hydroxide, potassium hydroxide, or mixtures thereof if a mineral acid was used, to obtain a pH of greater than or equal to 8. Alternatively, the aqueous layer is heated at a temperature and for a time sufficient, if carbon dioxide is used, to obtain a pH of equal to or greater than about 8. Typically, the layer will be heated to about 40 to about 85° C., preferably about 80° C. A gas, for example, air, methane or ethane is then blown through the solution at a rate sufficient to create a foam containing the surface active amines. The rate is readily determinable by the skilled artisan. The foam is then recovered to obtain the amine. The foam may be collapsed, or will collapse with time. Any gas which is unreactive in the instant process can be used for foam generation. The recovery process can be used either in the refinery or at the well head prior to reinjection.

The invention will now be illustrated by the following examples which are not meant to be limiting.

EXAMPLE 1

An alkyl ethoxylated ammonium salt of naphthenic acid was prepared by neutralizing a sample of commercial naphthenic acid with an equimolar amount of dodecyl pentaethanol amine. A 30 wt % solution of the salt was made in water to create a model emulsion containing alkyl ethoxylated ammonium naphthenate salt.

100 mL of the organic salt solution was taken in a separatory funnel and concentrated sulfuric acid added to bring the pH to 6. An instant release of naphthenic acid as a water insoluble oil was observed. The lower aqueous phase was separated from the oil phase and ammonium hydroxide added to obtain a pH of 9.

The aqueous solution was introduced into a foam generation apparatus as shown in FIG. 1. Air was bubbled through the inlet tube at the bottom. A copious foam was generated and collected in the collection chamber. The foam collapsed upon standing resulting in a yellow liquid characterized as a concentrate of dodecyl pentaethanol amine.

EXAMPLE 2

A North Sea crude, Gryphon having a TAN of 4.6 was subjected to an emulsion fractionation process as follows: The crude was treated with 2.5 molar equivalents of tertiary butyl diethanol amine and 10 wt % water for a time sufficient to form a water-in-oil emulsion of amine salt. The emulsion was separated into a plurality of layers and the layer containing amine salt emulsion was extracted and used as follows.

100 mL of the emulsion was taken in a separatory funnel and concentrated sulfuric acid added to bring it to a pH of 6. An instant release of naphthenic acid as a water insoluble oil was observed. The lower aqueous phase was separated from the oil phase. The oil phase was analyzed by FTIR and $^{13}C$ NMR to confirm the presence of naphthenic acids. HPLC analysis indicated 250 to 750 molecular weight naphthenic acids were extracted. Ammonium hydroxide was added to the aqueous phase to obtain a pH of 9. The aqueous solution was introduced into the foam generation apparatus shown in FIG. 1. Air was bubbled through the inlet tube at the bottom to generate a stable sustained foam that was collected in the collection chamber. The foam collapsed upon standing resulting in a yellow liquid characterized as a concentrate of tertiary butyl diethanol amine.

EXAMPLE 3

A North Sea Crude, Gryphon was subjected to the emulsion fractionation process described in Example 2. The amine salt emulsion phase was extracted and used as follows.

100 mL of the emulsion was taken into an autoclave, solid $CO_2$ added and the emulsion was stirred at 300 rpm at 80° C. and 100 psi for 2 hours. The product was centrifuged for 20 minutes at 1800 rpm to separate the water insoluble naphthenic acids from the aqueous phase. The oil phase was analyzed by FTIR and $^{13}C$ NMR to confirm the presence of naphthenic acid. HPLC analysis indicated 250 to 750 molecular weight naphthenic acids were extracted.

The lower aqueous phase was at a pH of 9 indicating regeneration of the organic amine. The aqueous solution was introduced into the foam generation apparatus shown in FIG. 1. Air was bubbled through the inlet tube at the bottom to generate a stable sustained foam that was collected in the collection chamber. The foam collapsed upon standing resulting in a yellow liquid characterized as a concentrate of tertiary butyl diethanol amine.

What is claimed is:

1. A method for recovering surface active amine from an emulsion comprising a salt of the amine and naphthenic acid comprising (a) contacting an emulsion layer or phase containing surface active amine salt with an acid selected from the group comprising mineral acids or carbon dioxide in an amount sufficient and under conditions to produce an amine salt of said mineral acid or an amine bicarbonate, wherein said surface active amine salt is produced via emulsion fractionation with said surface active amine (b) separating an upper layer and a lower aqueous layer; (c) adding, to the lower aqueous layer, an inorganic base if step (a) utilizes a mineral acid, or heating at a temperature and for a time sufficient if step (a) utilizes carbon dioxide, to raise the pH of the aqueous layer to greater than or equal to 8; (d) blowing gas through said aqueous layer to produce a foam containing said surface active amine; (e) recovering said foam containing said surface active amine.

2. The method of claim 1 wherein said emulsion is selected from the group of water-in-oil emulsions and oil-in-water emulsions.

3. The method of claim 1 wherein said mineral acid is selected from the group consisting of sulfuric acid, hydrochloric acid, phosphoric acid and mixtures thereof.

4. A method according to claim 1 wherein said surface active amines are alkyl oxyalkylated amines.

5. The method of claim 4 wherein said amines are selected from the group consisting of alkyl ethoxylated and alkyl propoxylated amines.

6. The method of claim 4 wherein said alkyl oxyalkylated amines are selected from the group consisting of ethoxylated and propoxylated amines.

* * * * *